US010172784B2

(12) United States Patent
Dueva-Koganov et al.

(10) Patent No.: US 10,172,784 B2
(45) Date of Patent: *Jan. 8, 2019

(54) BIOACTIVE COMPOSITONS HAVING SKIN ANTI AGING ACTIVITY

(71) Applicant: ISP Investments Inc., Wilmington, DE (US)

(72) Inventors: Olga V. Dueva-Koganov, White Plains, NY (US); Michael Koganov, White Plains, NY (US); Jeanette Richards, Liberty Township, OH (US); Tom Dawson, Hamilton, OH (US); Mary Jane Combs, Covington, KY (US)

(73) Assignee: ISP INVESTMENTS LLC, Wilmington, DE (US)

( * ) Notice: Subject to any disclaimer, the term of this patent is extended or adjusted under 35 U.S.C. 154(b) by 839 days.

This patent is subject to a terminal disclaimer.

(21) Appl. No.: 14/366,968

(22) PCT Filed: Dec. 19, 2012

(86) PCT No.: PCT/EP2012/076132
§ 371 (c)(1),
(2) Date: Jun. 19, 2014

(87) PCT Pub. No.: WO2013/092699
PCT Pub. Date: Jun. 27, 2013

(65) Prior Publication Data
US 2014/0348766 A1 Nov. 27, 2014

Related U.S. Application Data

(60) Provisional application No. 61/579,197, filed on Dec. 22, 2011.

(51) Int. Cl.
| | | |
|---|---|---|
| A61K 8/97 | (2017.01) |
| A61K 36/28 | (2006.01) |
| A61K 36/05 | (2006.01) |
| A61K 36/82 | (2006.01) |
| A61K 36/23 | (2006.01) |
| A61Q 19/04 | (2006.01) |
| A61Q 19/08 | (2006.01) |
| A61K 8/9789 | (2017.01) |
| A61K 8/9711 | (2017.01) |

(52) U.S. Cl.
CPC .............. A61K 8/97 (2013.01); A61K 8/9711 (2017.08); A61K 8/9789 (2017.08); A61Q 19/04 (2013.01); A61Q 19/08 (2013.01)

(58) Field of Classification Search
CPC ................................ A61K 36/28; A61K 36/82
USPC .......................................... 424/729, 763, 773
See application file for complete search history.

(56) References Cited

U.S. PATENT DOCUMENTS

| | | | |
|---|---|---|---|
| 2,809,971 | A | 10/1957 | Bernstein et al. |
| 3,236,733 | A | 2/1966 | Karsten et al. |
| 3,753,196 | A | 8/1973 | Kurtz et al. |
| 3,755,560 | A | 8/1973 | Dickert et al. |
| 3,761,418 | A | 9/1973 | Parran et al. |
| 4,323,683 | A | 4/1982 | Bolich, Jr. et al. |
| 4,345,080 | A | 8/1982 | Bolich, Jr. |
| 4,379,753 | A | 4/1983 | Bolich, Jr. |
| 4,421,769 | A | 12/1983 | Dixon et al. |
| 4,470,982 | A | 9/1984 | Winkler |
| 5,686,082 | A | 11/1997 | N'Guyen |
| 5,686,367 | A | 11/1997 | Hayashi |
| 7,473,435 | B2 | 1/2009 | Koganov |
| 7,537,791 | B2 | 5/2009 | Koganov |
| 2003/0175235 | A1 | 9/2003 | Koganov |
| 2004/0175347 | A1 | 9/2004 | Bissett |
| 2005/0048008 | A1 | 3/2005 | Gupta |
| 2005/0181079 | A1 | 8/2005 | Koganov |
| 2006/0275237 | A1 | 12/2006 | Bissett et al. |
| 2008/0064723 | A1 | 3/2008 | Ideta et al. |
| 2009/0123406 | A1 | 5/2009 | Pheiffer |
| 2010/0120871 | A1 | 5/2010 | Dawson, Jr. et al. |
| 2011/0110872 | A1 | 5/2011 | Koganov et al. |
| 2014/0341829 | A1 | 11/2014 | Dueva-Koganov et al. |

FOREIGN PATENT DOCUMENTS

| | | | |
|---|---|---|---|
| CN | 101559181 A | * | 10/2009 |
| DE | 41 18 098 C1 | | 5/1992 |
| EP | 1 262 167 A1 | | 12/2002 |
| EP | 1 543 822 A1 | | 6/2005 |
| EP | 1 543 823 A1 | | 6/2005 |
| EP | 1 806 121 A1 | | 7/2007 |
| FR | 2 946 886 A1 | | 12/2010 |
| JP | 2002-020243 A | | 1/2002 |
| JP | 2002-332240 A | | 11/2002 |
| JP | 2005-296352 A | | 10/2005 |
| JP | 2006-008536 A | | 1/2006 |

(Continued)

OTHER PUBLICATIONS

Morioka et al, "Effects of Zinc on the New Preparation Method of Hydroxy Double Salts," Inorganic Chemistry, vol. 38, No. 19, pp. 4211-4216 (1999).

Crepaldi et al., "Chemical, Structural, and Thermal Properties of Zn(II)-Cr(III) Layered Double Hydroxides Intercalated with Sulfated and Sulfonated Surfactants," Journal of Colloid and Interface Science 248, pp. 429-442 (2002).

"Cosmetic material for conditioning skin and hair—comprises compounded Japanese parsley extracts with extracts of specific Rosaceae plants," WPI Wolrd Patent Information Derwent, vol. 26, No. 88, May 20, 1988, XP002041404, abstract.

(Continued)

Primary Examiner — Christopher R Tate
Assistant Examiner — Deborah A Davis
(74) Attorney, Agent, or Firm — William J. Davis

(57) ABSTRACT

The present invention relates to bioactive compositions comprising blends of camellia and feverfew serum fractions and/or kelp and parsley serum fractions.

20 Claims, 7 Drawing Sheets

(56) References Cited

FOREIGN PATENT DOCUMENTS

| JP | 2008-137998 A | 6/2008 |
|---|---|---|
| KR | 10-2009-0009559 A | 1/2009 |
| WO | 02/074280 A1 | 9/2002 |
| WO | 2007/098471 A2 | 8/2007 |
| WO | 2010/054343 A2 | 5/2010 |

OTHER PUBLICATIONS

Notification of Transmittal of the International Search Report and the Written Opinion of the International Searching Authority, or the Declaration from the International Bureau of WIPO for International Application No. PCT/EP2012/076132 dated Nov. 15, 2013.
McCutcheon, Emulsifiers & Detergents, North American Edition, pp. 317-324 (1986).

* cited by examiner

| Serum Fraction/Blend | Lot # | Dry wt | pH | Blend Preparation (serum fraction parts added) |
|---|---|---|---|---|
| Kelp | 0320J/MS-0363 | 4.80% | 5 | N/A |
| Kelp | 0320J/MS-0492 | 4.70% | 4.7 | N/A |
| Kelp | 0320J/MS-0492-01 | 4.70% | 4.7 | N/A |
| Kelp | MP0726M/MS-0571 | 4.70% | 5.1 | N/A |
| Parsley | PA1117L/HP-0499 | 4.50% | 3.9 | N/A |
| Parsley | PA1117L/HP-0570 | 4.50% | 4.1 | N/A |
| Kelp-Parsley 10:90 | B19-0729M/OS-0572 | 4.30% | 4.1 | 1 Part Kelp + 9 Parts Parsley |
| Kelp-Parsley 20:80 | B19-0729M/OS-0573 | 4.30% | 4.1 | 2 Parts Kelp + 8 Parts Parsley |
| Kelp-Parsley 30:70 | B19-0729M/OS-0574 | 4.30% | 4.1 | 3 Parts Kelp + 7 Parts Parsley |
| Kelp-Parsley 40:60 | B19-0729M/OS-0575 | 4.30% | 4.1 | 4 Parts Kelp + 6 Parts Parsley |
| Kelp-Parsley 50:50 | B19-0215M/OS-0529 | 4.50% | 4 | 1 Part Kelp +1 Part Parsley |
| Kelp-Parsley 50:50 | B19-0712M/OS-0563 | 4.50% | 4 | 1 Part Kelp +1 Part Parsley |
| Kelp-Parsley 50:50 | B19-0729M/OS-0576 | 4.30% | 4.2 | 5 Parts Kelp + 5 Parts Parsley |
| Kelp-Parsley 60:40 | B19-0729M/OS-0577 | 4.50% | 4.3 | 6 Parts Kelp + 4 Parts Parsley |
| Kelp-Parsley 70:30 | B19-0729M/OS-0578 | 4.40% | 4.3 | 7 Parts Kelp + 3 Parts Parsley |
| Kelp-Parsley 80:20 | B19-0729M/OS-0579 | 4.40% | 4.5 | 8 Parts Kelp + 2 Parts Parsley |
| Kelp-Parsley 90:10 | B19-0729M/OS-0580 | 4.50% | 4.7 | 9 Parts Kelp + 1 Part Parsley |
| Camellia | TECJ062904-0184 | 8.10% | 4 | N/A |
| Camellia | TECJ062904-0184-01 | 8.10% | 4.1 | N/A |
| Camellia | TECJ062904-0161-01 | 7.50% | 4.1 | N/A |
| Camellia | TECJ062904-0554 | 7.40% | 4.2 | N/A |
| Feverfew | FF0811K/TL | 8.20% | 3.9 | N/A |
| Camellia-Feverfew 20:80 | FFCSWASC02P-0351 | 7.60% | 3.8 | 2 Parts Camellia + 8 Parts Feverfew |
| Camellia-Feverfew 20:80 | FFCSWASC02P-0351-01 | 7.60% | 3.9 | 2 Parts Camellia + 8 Parts Feverfew |
| Camellia-Feverfew 20:80 | B02-0712M/OS-0562 | 7.50% | 3.4 | 1 Part Camellia + 4 Parts Feverfew |
| Camellia-Feverfew 50:50 | B02-0712M/OS-0561 | 7.50% | 3.6 | 1 Part Camellia + 1 Part Feverfew |
| Camellia-Feverfew 80:20 | B02-0719M/OS-0567 | 7.50% | 4.1 | 4 Parts Camellia + 1 Part Feverfew |

FIG. 7

BIOACTIVE COMPOSITONS HAVING SKIN ANTI AGING ACTIVITY

FIELD OF THE INVENTION

The present invention relates to the field of topical applications of skin care compositions to the skin. The invention further relates to skin care compositions comprising blends of camellia and feverfew serum fractions and/or kelp and parsley serum fractions. The invention also relates to methods for increasing melanin production in skin by topically applying the skin care composition to areas thereof in order to stimulate one or more steps in melanin synthesis.

BACKGROUND OF THE INVENTION

Human skin comprises three principal layers: the epidermis, the dermis, and the subcutaneous fat layer. The epidermis comprises four layers (from external to internal): the stratum corneum, the granular layer, the spiny layer, and the basal layer. A separate fifth layer, the stratum lucidum, may be present between the stratum corneum and granular layer. The basal layer produces cells which gradually migrate outward to form the other epidermal layers. As these cells migrate outward, they lose their central nucleus and start to produce skin proteins (keratins) and fats (lipids). These cells are identified as keratinocytes when present in the upper layers of the epidermis. Melanocytes are another class of cells located in the basal layer of the epidermis. Melanocytes are responsible for the production of melanin, which is primary factor in skin pigmentation.

Melanin is produced by a complex set of reactions within the melanocyte involving, at a basic level, the enzyme tyrosinase and L-tyrosine as a substrate. Tyrosinase catalyzes the conversion of L-tyrosine to DOPA (L-3,4-dihydroxyphenylalanine) and of DOPA to dopaquinone. Dopaquinone undergoes further conversion to form melanin. Melanin aggregates in organelles known as the melanosomes which are transferred to keratinocytes along slender filaments of the melanocyte known as dendrites. There are approximately 1500 gene products expressed in melanosomes with 600 of them being expressed at any given time and 100 of them believed to be unique to the melanosome. In addition, there are many regulatory elements involved in signaling, in the transport of melanosomes within the melanocyte, and in the transfer of melanosomes to the keratinocytes.

The production of melanin can be triggered by a variety of external and internal events. For example, melanocytes produce additional melanin when skin is subjected to UV radiation. The melanin is then transported via melanasomes to the keratinocytes, which then leaves the skin with a pigmented or "tanned" appearance. However, chronic UV exposure may lead to more subtle changes in skin tone. Often these changes are described as uneven tone or as a mottled appearance. Moreover, inflammation-related skin disorders such as atopic dermatitis or post-inflammatory hypopigmentation can also leave the skin with uneven tone appearance.

On the other hand, melanin is able to absorb electromagnetic irradiation especially the wavelengths of UV radiation. Furthermore, melanin acts as a scavenger for radicals. Thus, melanin is generally considered as a natural skin filter for UV radiation. Thus, there is a desire to provide compositions and methods of treatment that can improve the appearance of unevenly toned skin and provide a uniformly tanned appearance, which may provide an aesthetic benefit (e.g., perceived younger appearance than chronological age) in addition to providing protection against UV radiation-induced skin damage.

Over recent years, consumers have increasingly demanded "natural" cosmetic products. As a result, cosmetic manufacturers have incorporated more plant-based materials into their cosmetic formulations. Although various plants have been used for hundreds or even thousands of years for a variety of reputed indications, until recent times it has not been possible to clinically verify purported effectiveness or to identify new potential uses based upon the underlying science of the plant's bioactivity. With recent advances in science, researchers are now better able to assess the efficacy and/or potential new uses for plants that until recently were only supported by folklore. Because of the newness of the science, and because the number of plants that could potentially be utilized as cosmetic bioactives is so immense, the vast majority of plants have not yet been fully investigated.

Many of the methods used for extracting botanical components from plants involve techniques that are harmful to the plant tissue composition and/or the bioactive components of interest contained in that tissue. Consequently, traditional extraction methods often fail to deliver the full spectrum of activities that exist within a plant cell and thus the full potential of botanical-based cosmetic formulations is not realized. In addition, many traditional extraction methods utilize harsh chemical solvents, which are not "natural" and thus are materials that consumers want to avoid applying to their skin. Furthermore, these solvent-based processes produce toxic chemical wastes that can harm the environment if not properly handled and disposed of as hazardous waste.

Moreover, just because a material is "natural" does not guarantee that it is free from undesired substances that would make the material suitable for use on skin, however. For example, many plants contain photosensitizers such as pheophorbides and/or contact allergens such as proteins. At levels naturally found in many common plants, pheophorbides and/or proteins do not cause concern for most people. However, when plant materials are condensed to a highly concentrated form, such as through extraction, these materials can be present at levels that cause skin irritation and allergic reactions, including rashes. Even when these materials are present at their natural levels, however, there are still many sensitive individuals who experience negative skin reactions.

Furthermore, as demands for natural products have increased, so have concerns about protecting earth's natural resources. Many of the "natural" ingredients that consumers desire are derived from bioresources that are depleted and/or destroyed when harvested for use in consumer products. Thus, consumers' desire for natural, more earth-friendly products can ironically lead to the destruction of the very bioresources they aim to preserve. Thus, there is a need for natural bioactive botanical compositions that maintain their spectrum of desired bioactivity, are suitable for topical skin application, and are not prepared using harsh chemical solvents. Furthermore, there is a need for cosmetic compositions containing such bioactives that are effective for improving the appearance of skin pigmentation. In addition, there is a need for such bioactive materials that can be harvested and processed in an ecologically sound, sustainable manner.

These and other objects of the present invention will become apparent in light of the following disclosure.

SUMMARY OF THE INVENTION

The present invention relates to skin care compositions and methods that can help increase melanin production in skin by topically applying the skin care composition to areas thereof in order to stimulate one or more steps in melanin synthesis, which may provide an aesthetic benefit (e.g., perceived younger appearance than chronological age) in addition to providing protection against UV radiation-induced skin damage. According to an embodiment, a skin care composition suitable for darkening regions of mammalian skin is provided. The skin care composition comprises an effective amount of a first composition comprising a combination of a camellia serum fraction and a feverfew serum fraction, or a second composition comprising a combination of a parsley serum fraction and a kelp serum fraction; and a dermatologically acceptable carrier. According to another embodiment, a method for reducing the appearance of skin hypopigmentation is provided. The method comprises topically applying a skin care composition to a skin surface, wherein the skin care composition is applied for a period of time sufficient to stimulate one or more steps in melanogenesis (melanin synthesis). The skin care composition comprises an effective amount of a first composition comprising a combination of a camellia serum fraction and a feverfew serum fraction, or a second composition comprising a combination of a parsley serum fraction and a kelp serum fraction; and a dermatologically acceptable carrier.

According to another embodiment, a method for reducing the appearance of skin hypopigmentation is provided. The method comprises topically applying a skin care composition to a skin surface, wherein the skin care composition is applied for a period of time sufficient to stimulate one or more steps in melanogenesis (melanin synthesis). The skin care composition comprises an effective amount of a combination of a camellia serum fraction, a feverfew serum fraction, a parsley serum fraction, and a kelp serum fraction; and a dermatologically acceptable carrier.

According to one aspect of the present invention, a method is provided that comprises topically applying the skin care composition comprising an effective amount of a synergistic combination of skin tone agents to a skin surface for the purpose of improving the appearance of skin tone.

In response to the technical problems identified in the background, the present invention may take other forms. Further forms of the present invention will be appreciated in the detailed description that follows.

BRIEF DESCRIPTION OF THE DRAWINGS

It is believed that the present invention will be better understood from the following description taken in conjunction with the accompanying drawings. The referenced drawings are not to be construed as limiting the scope of the present invention.

FIG. 7 is a table showing the identity of the serum fractions and blends used herein.

DETAILED DESCRIPTION OF THE INVENTION

Figure 1:
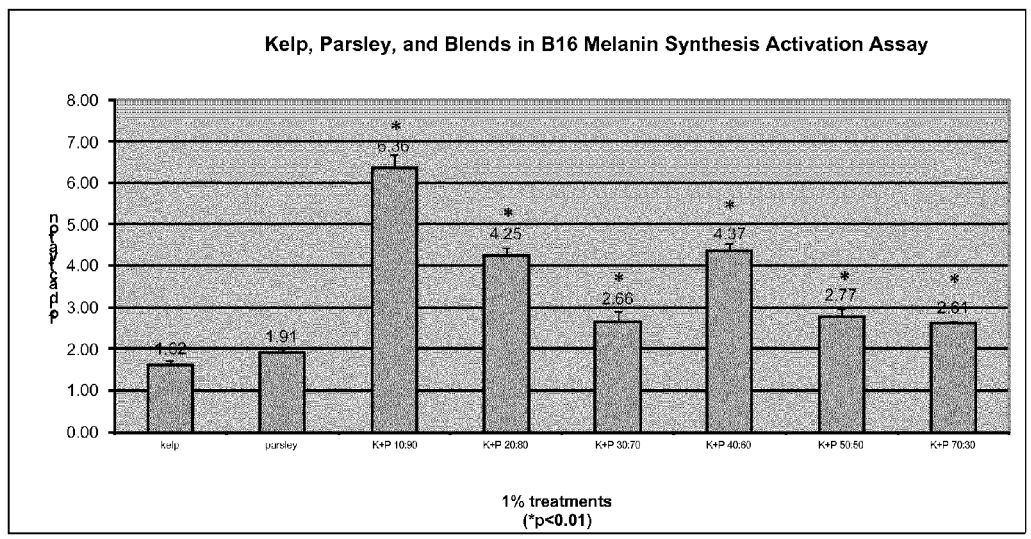
FIG. 1 is a bar graph showing melanin synthesis activation when kelp and parsley serum fractions are evaluated separately and as varied blends in a melanocyte assay.
Figure 2:
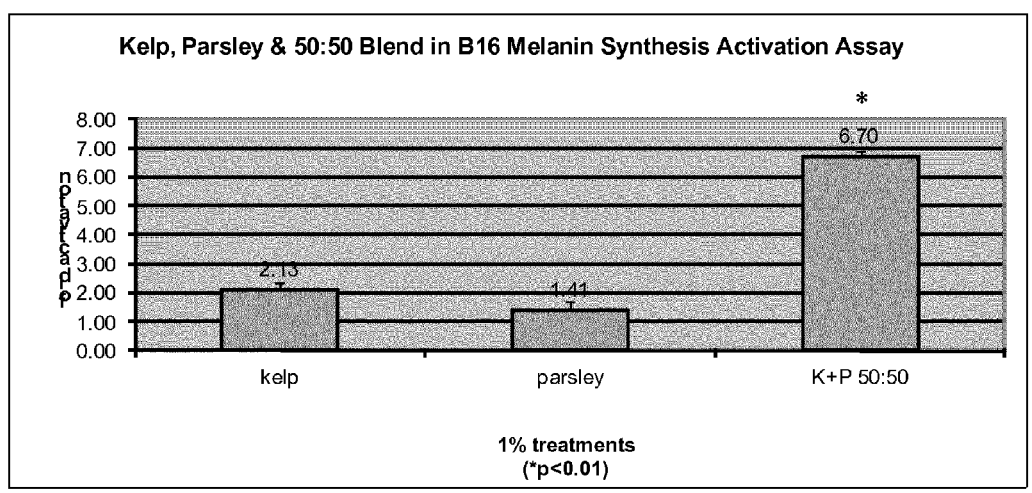
FIG. 2 is another bar graph showing melanin synthesis activation when kelp and parsley serum fractions are evaluated separately and as a 50:50 blend in a melanocyte assay.
Figure 3:
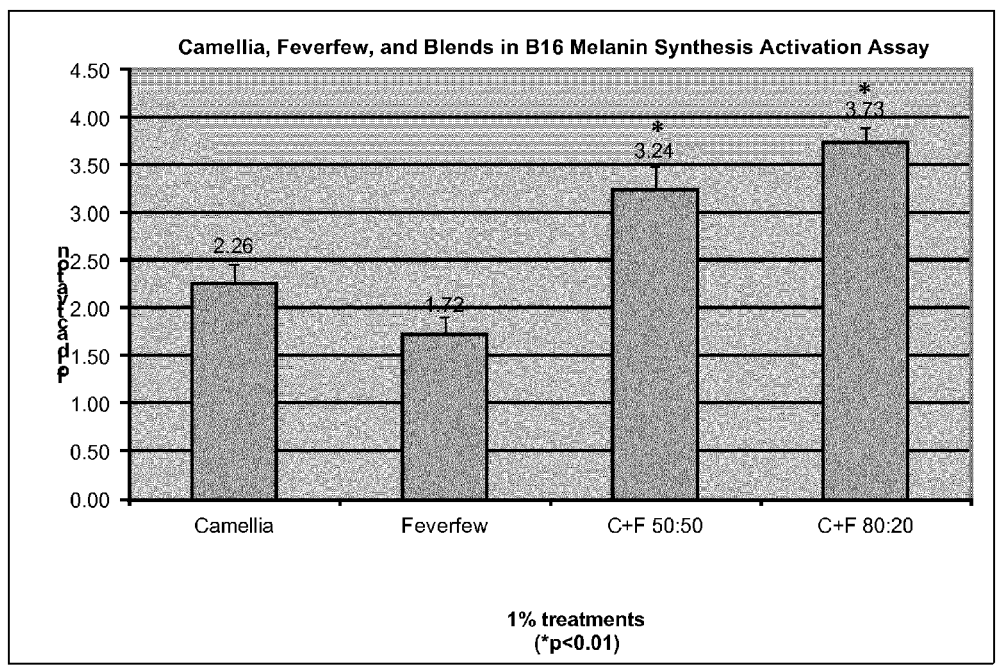
FIG. 3 is a bar graph showing melanin synthesis activation when camellia and feverfew serum fractions are evaluated separately and as varied blends in a melanocyte assay.
Figure 4:
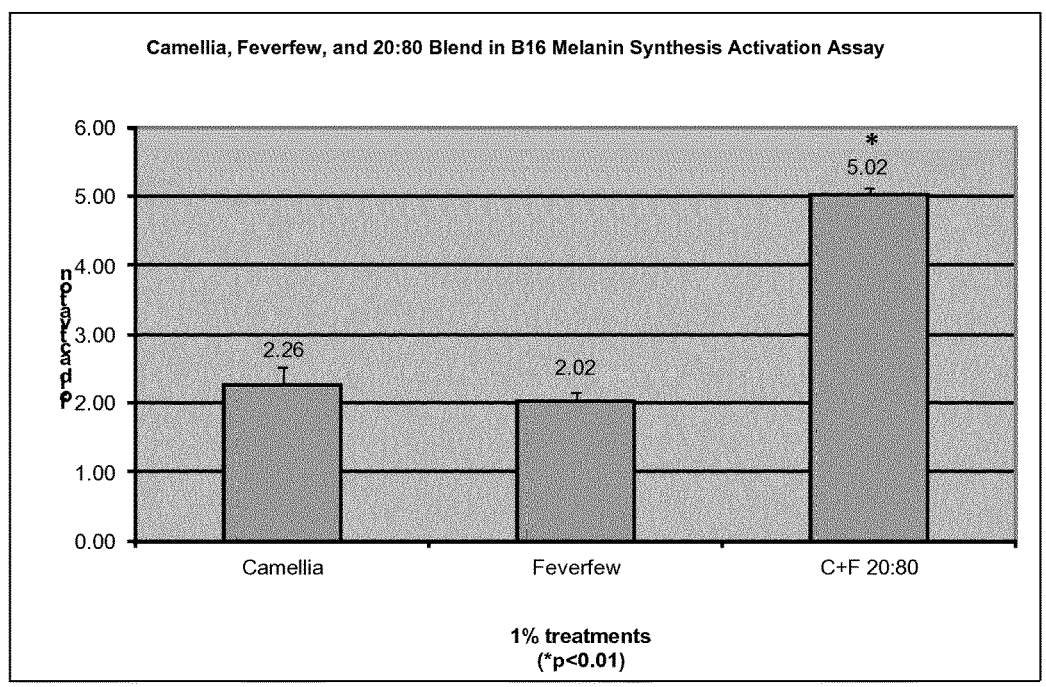
FIG. 4 is another bar graph showing melanin synthesis activation when camellia and feverfew serum fractions are evaluated separately and as 20:80 blend in a melanocyte assay.
Figure 5:
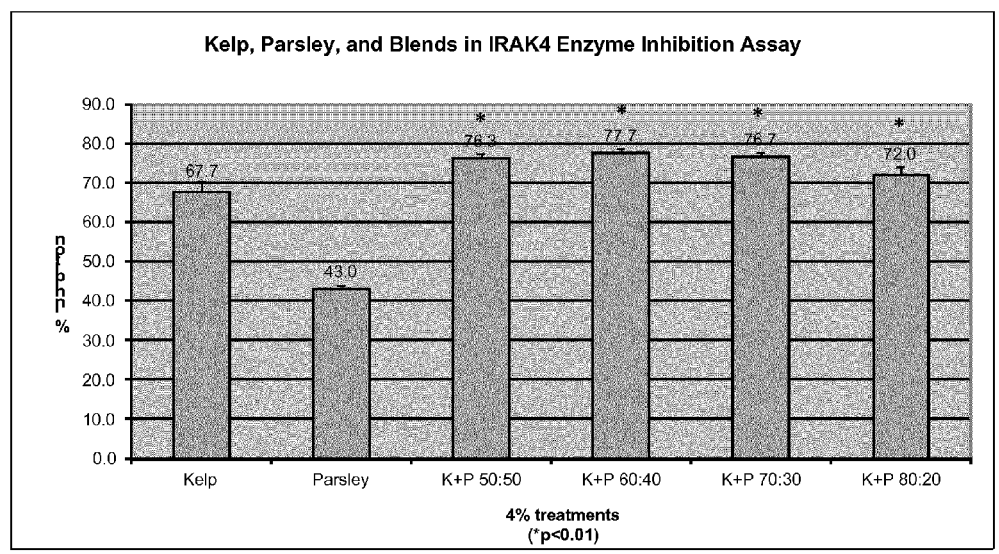
FIG. 5 is a bar graph showing inhibition of interleukin-1 receptor-associated kinase (IRAK-4) when kelp and parsley serum fractions are evaluated separately and as varied blends in an ADP-Glo™ assay.
Figure 6:
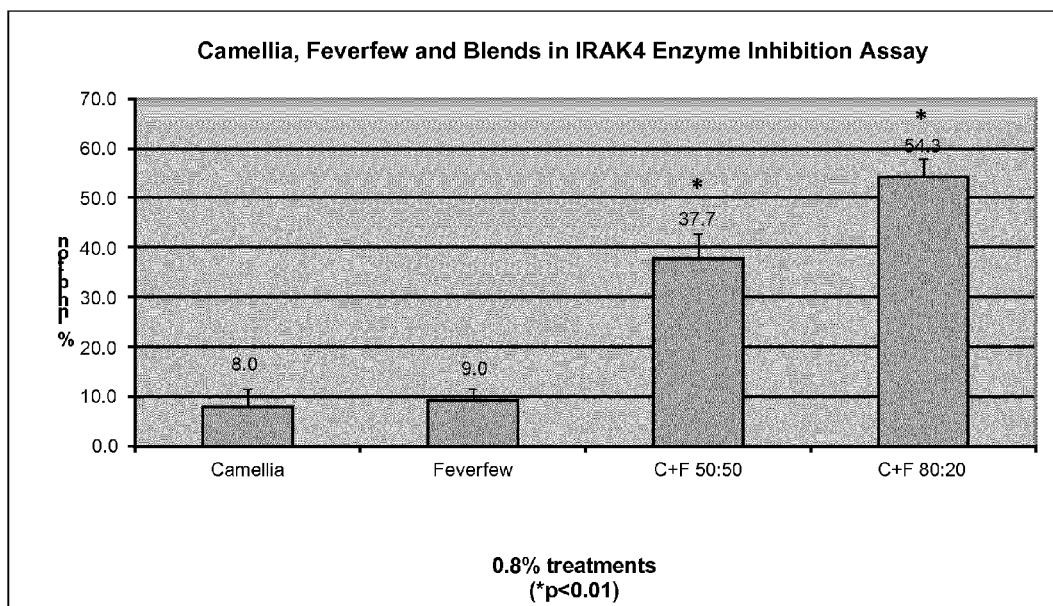
FIG. 6 is a bar graph showing inhibition of IRAK-4 when camellia and feverfew serum fractions are evaluated separately and as varied blends in an ADP-Glo™ assay.

All percentages and ratios used herein are by weight of the total composition and all measurements made are at 25° C., unless otherwise designated. All numeric ranges are inclusive of narrower ranges; delineated upper and lower range limits are interchangeable to create further ranges not explicitly delineated.

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods.

The term "apply" or "application" as used in reference to a composition, means to apply or spread the compositions of the present invention onto a mammalian skin surface such as the epidermis.

The term "dermatologically acceptable" as used herein means that the compositions or components described are suitable for use in contact with human skin tissue without undue toxicity, incompatibility, instability, allergic response, and the like.

The term "effective amount" as used herein means an amount of a compound or composition sufficient to significantly induce a positive benefit.

The term "post-inflammatory hypopigmentation" as used herein refers to an acute to chronic decrease in pigmentation as a response to a transient inflammatory event.

The term "hypopigmented spot" as used herein refers to a defined area of skin wherein the pigmentation is less than that of an adjacent area of skin due to localized and chronic or systemic underproduction of melanin.

The term "skin tone agent" as used herein refers to an agent that regulates melanin production signals, synthesis of melanin, systemic transfer of melanin between the melanocyte and the keratinocyte, and/or melanin degradation. Skin tone agents can improve the appearance of uneven skin tone by acting as a pigmentation enhancing cosmetic agent.

The term "skin tone" as used herein refers to the overall appearance of melanin in the skin caused by the systemic, rather than transient, synthesis of melanin. Skin tone is typically characterized over a larger area of the skin. The area ideally may be than 100 mm$^2$, but larger areas are envisioned such as the entirety of the facial skin or any of the facial skin surfaces. Skin tone can be measured by image analysis. For example, overall lightness can be measured by L* coordinate in L*a*b* color space (International Commission on Illumination). Chromophore mapping such as melanin mapping and melanin concentration may be used as an indicator of overall skin tone. Mean melanin may be calculated from the chromophore map data. Additionally, skin tone evenness can be determined by melanin evenness which also may be calculated from the chromophore map data. Suitable chromophore mapping techniques are discussed in the example below.

The term "facial skin surface" as used herein refers to one or more of forehead, periorbital, cheek, perioral, chin, and nose skin surfaces.

As used herein, "exogenous solvent" means any solvent that is not inherently present in the plant material, but is placed in contact with the plant material for the purpose of separating (e.g., extracting) compounds from the plant material.

The term "serum fraction," as used herein, means a composition produced by a general method comprising the steps of: (a) grinding and pressing of fresh plant matter and (b) separating a liquid fraction from a cell wall fraction to obtain fresh cell juice, wherein no exogenous liquid is added prior or during said separating; (c) filtering the fresh cell juice to obtain a first filtrate; and (d) fractionating the first filtrate to obtain the serum fraction.

I. Skin Care Compositions

An embodiment of the present invention relates to various compositions and, more specifically, to compositions for application to a skin surface, which does do not include a scalp surface. The skin care compositions comprise an effective amount of skin tone agents, which are effective for providing evenly toned skin, and a dermatologically acceptable carrier. The compositions may be in a wide variety of product forms that include, but are not limited to, solutions, suspensions, lotions, creams, gels, toners, sticks, pencil, sprays, aerosols, ointments, cleansing liquid washes and solid bars, skin conditioners, pastes, foams, powders, mousses, shaving creams, wipes, strips, patches, electrically-powered patches, wound dressing and adhesive bandages, hydrogels, film-forming products, facial and skin masks (with and without insoluble sheet), make-up such as foundations, and eye shadows, and the like. The composition form may follow from the particular dermatologically acceptable carrier chosen.

A. Skin Tone Agents

The skin care compositions in accordance to embodiments of the present invention comprise an effective amount of a combination of skin tone agents which are blends of serum fractions. Accordingly, in an embodiment, the skin care composition comprises a first combination of a camellia serum fraction and a feverfew serum fraction; or a second combination of a parsley serum fraction and a kelp serum fraction. According to another embodiment the skin care composition comprises the first and the second combinations.

The camellia, feverfew, or parsley fractions each consist essentially of the flower, leaf, and/or stem serum fractions obtained from plants belonging to *camellia sinensis, chrysanthemum parthenium,* or *petroselinum crispum,* respectively, and the kelp serum fraction consists essentially of a serum fraction from a photosynthetic organism *macrocystis pyrifera,* which is commonly known as brown algae. For purposes of simplifying the discussion herein, brown algae should be understood to be inclusive to "plant" or "plants" or "biomass" when referencing the source of a serum fraction. Exemplary serum fractions used herein are provided by Akzo Nobel Surface Chemistry LLC, Chicago, Ill. Exemplary serum fraction preparation methods are set forth in U.S. Pat. No. 7,473,435 (e.g., for camellia), U.S. Pat. No. 7,537,791 (e.g., for parthenolide free bioactive ingredients from feverfew (*Tanacetum parthenium*)), and U.S. Patent Application Publication No. 2011/0110872 (e.g., for kelp), which are incorporated herein by reference in their entirety. The serum fractions may be blended to form a combination of serum fractions that surprisingly produce synergistic effects, as discussed further below.

The general method for preparing a serum fraction comprises the steps of: grinding and pressing of clean, fresh plant matter; separating a liquid fraction from a cell wall fraction to obtain fresh cell juice, wherein no exogenous liquid is added prior or during said separating; filtering the fresh cell juice to obtain a first filtrate; and fractionating the first filtrate to obtain the serum fraction for use herein. Fractionating may include one or more of the following steps: adjusting pH; heating such as microwaving; filtering and/or centrifuging to remove chlorophyll, pigments, and/or proteins from said first filtrate to form the serum fraction. The method may further include stabilizing to serum fraction. Stabilizing may include adding preservatives and incubating the mixture until complete solubilization of the preservative is achieved. Exemplary preservatives include one or more of potassium sorbate, sodium benzoate, sodium methyl paraben, and/or citric acid.

The resulting combinations or blends of serum fractions have superior bioactivity versus traditionally prepared plant extracts. Unlike traditional extracts, the serum fraction is prepared from fresh plant cell juice that has been mechanically separated from the rest of the fresh plant material. Importantly, no exogenous solvent (e.g., water, hexane, acetone, ethanol) is added during the juice separation process. The resulting cell juice contains the full spectrum of compounds found in fresh plant matter, thus the resulting serum fractions contain a much broader range of active compounds than do traditional plant extracts, which contain only the narrow range of compounds that can be separated with a particular solvent.

Furthermore, using fresh plants maintains the integrity of the bioactive components inherently present in the fresh plant matter. Traditional plant extracts are not prepared from fresh plant matter, but rather from dried plant material, which has undergone degradation due to dehydration. During dehydration, the cell walls are compromised, causing the degradation of compounds through mechanisms such as hydrolysis, oxidation, polymerization, Maillard reactions, and isomerization. When the dried leaves are extracted, the resulting extract thus contains these degradation products that were not originally present in the fresh plant matter. Accordingly, the composition of the resulting dry leaf extract greatly differs from that of fresh juice and the resulting serum fraction.

An exemplary preparation of a *camellia sinensis* serum fraction is described in U.S. Pat. No. 7,473,435, and is summarized below. The serum fraction from *camellia sinensis* plants can be prepared by a method comprising the steps of (1) biomass preparation; (2) grinding, maceration, and pressing of plant biomass; (3) separation of a membrane fraction from the cell juice to provide a cell juice supernatant; (4) separation of a cytoplasm fraction from the cell juice supernatant; and (5) isolation of the serum fraction.

(1) Biomass Preparation: Sufficient amounts of fresh camellia (*camellia sinensis*) plant biomass (only top tender young leaf tissue with buds) are harvested to yield approximately 100 kg of dry matter. The level of dry matter in the fresh biomass is calculated to be 21.70 wt %, requiring harvesting of approximately 461 kg of fresh plant biomass to yield 100 kg of dry matter. Care is taken to preserve the inherent moisture content of the plant biomass and to avoid wilting due to moisture loss. The harvesting is conducted in such a manner as to avoid or minimize chopping, mashing, and crushing of the collected biomass to avoid the disruption of the leaf cell structure, which can induce endogenous enzymatic reactions catalyzed by phenol-oxidase and peroxidase. Because these reactions are intensified with the time of oxidation, all steps are completed in the shortest possible period of time. For example, the harvested biomass is delivered for processing not more than 10 minutes after cutting. This is done to minimize exposure of the plant biomass to sun, high temperature, and other negative environmental factors. A washing step is performed to remove soil particles and other debris from the plants prior to further processing. This washing is accomplished by washing the harvested plants for ≤5 minutes in ≤1 kg/cm² water pressure. The residual water wash does not contain any green or brown pigments, indicating proper water pressure and washing duration. The excess water is removed from the washed plant biomass.

(2) Grinding, Maceration, and Pressing of Plant Biomass: After harvesting, collecting, and washing the plant biomass, the plants then undergo grinding, maceration, and pressing to extract the intracellular content (i.e., the plant cell juice) and to separate the plant cell juice from the fiber-enriched cell walls fraction (cell walls fraction). A hammer mill (Model VS 35, Vincent Corporation, Fla.) having 10 HP engine and set of screens may be used to grind the biomass to yield plant tissue particles of suitably small size in a shortest amount of time and without significant increase of biomass temperature. The hammer mill can be set to produce the maximum size of macerated plant particles of ≤0.5 centimeters during ≤10 seconds of treatment. The biomass temperature is increased only ≤5° C. A horizontal continuous screw press (Compact Press "CP-6", Vincent Corporation, Fla.) is immediately used to extract the plant cell juice from the plant. The pressure on the cone of the screw press is maintained at a level of 24 kg/cm², with a screw speed of 12 rpm and only a temperature increase of ≤5° C. This treatment can yield about 276 kg of plant cell juice having dry mater level of about 8.5 wt %.

(3) Separation of the Membrane Fraction from the Cell Juice: The initial plant cell juice having dry matter level of about 8.5 wt % contains small fiber particles, which can be removed by filtration through four layers of nylon fabric or by using low-speed centrifugation biomass. The filtered plant cell juice is exposed to microwave treatment using a temperature probe control. This treatment continues until the temperature of the cell juice reached 60° C. Once coagulation is induced, the treated cell juice is immediately cooled to 40° C. Separation of the membrane fraction from the coagulated cell juice is achieved using centrifugation at greater than or equal to 3,000 g for greater than or equal to 20 minutes. This yields a membrane fraction (precipitate) and a cell juice supernatant, which contains a cytoplasm fraction and a cell serum fraction (which contains low molecular weight soluble components). The cell juice supernatant is used for further processing to yield a serum fraction.

(4) Separation of the Cytoplasm Fraction from the Cell Juice Supernatant: In order to separate out the cytoplasm fraction, the cell juice supernatant is subjected to isoelectric precipitation. Precipitation of the cytoplasm fraction is induced using a titration method utilizing 5.0N Hydrochloric Acid (HCl) to bring the pH of the cell juice supernatant to about 4. The separation of precipitated cytoplasm fraction, which may have a dry matter level of about 14.5 wt %, from supernatant is achieved by centrifugation at greater than or equal to 3,000 g (where g is the relative centrifugal force) for greater than or equal to 20 minutes.

(5) Isolation of the Serum Fraction: After separation of the cytoplasm fraction, the supernatant contains suspended particles. In order to separate out these particles, the supernatant is centrifuged at greater than or equal to 7,500 g for greater than or equal to 30 minutes. The transparent supernatant is filtered through a filter having 0.8 micrometer pores. This filtrate (*camellia sinensis* serum fraction) can have a dry matter level of about 5.7 wt %, which is based on the recited process using no exogenous extraction solvents.

It can be appreciated that the dry matter level of the serum fraction can vary depending on a variety of factors such as the moisture content of the plant biomass, which itself may have variations based on seasonal and/or geographical source. Accordingly, in one embodiment the dry matter level in the camellia serum fraction can range from about 0.1 wt % to about 25 wt %, from about 1 wt % to about 15 wt %, from about 2 wt % to about 10 wt %, or from about 3 wt % to about 9 wt %, for example. In one embodiment, the dry matter level in the feverfew fraction can range from about 0.1 wt % to about 25 wt %, from about 1 wt % to about 15 wt %, from about 2 wt % to about 10 wt %, or from about 3 wt % to about 9 wt %, for example. In one embodiment, the dry matter level in the kelp fraction can range from about 0.1 wt % to about 25 wt %, from about 1 wt % to about 15 wt %, from about 2 wt % to about 10 wt %, or from about 3 wt % to about 9 wt %, for example. In one embodiment, the dry matter level in the parsley fraction can range from about 0.1 wt % to about 25 wt %, from about 1 wt % to about 15 wt %, from about 2 wt % to about 10 wt %, or from about 3 wt % to about 9 wt %, for example. In another embodiment, the dry matter level in the blend of the kelp and parsley serum fractions and/or the camellia and feverfew serum fractions can range from about 0.1 wt % to about 25 wt %, from about 1 wt % to about 15 wt %, from about 2 wt % to about 10 wt %, or from about 3 wt % to about 9 wt %, for example.

Additionally, the serum fractions can be further characterized with respect to the content of specified compounds or classes of compounds in the serum fraction and/or the dry matter, or by the absence of other compounds or class of compounds. For example, in one embodiment, the camellia serum fraction can have a total catechin content of between about 8.0 and about 20.0 milligrams per gram of dry matter, particularly between about 10.0 and about 18.0 milligrams per gram of dry matter, and more particularly between about 12.0 and about 16.0 milligrams per gram of dry matter. In another example, the feverfew serum fraction is either free of, or substantially free of, α-unsaturated γ-lactones, such as parthenolide.

Similar, analysis and characterization can applied to the feverfew (see e.g., U.S. Pat. No. 7,537,791), kelp (see e.g., U.S. Patent Application Publication No. 2011/0110872), and parsley serum fractions.

In some instances, a serum fraction cannot be used as an active ingredient of topical products due to a lack of stability and deterioration of color and odor. A refinement of the serum fraction may involve the following steps: heat treatment, cooling, filtration, and stabilization. Refinement can be performed immediately after separation of the serum fraction from the cytoplasm fraction. For example, the camellia serum fraction is exposed to microwave treatment using a temperature probe control. This treatment continues until the temperature of the serum fraction reaches 99° C. (90° C. is required as was previously described in U.S. Pat. No. 7,537,791, which is hereby incorporated by reference in its entirety). Once coagulation is induced, the treated serum fraction is immediately cooled to 10° C. The coagulated serum fraction is vacuum filtrated through filter having porous 0.8 micrometer (double layers of Whatman No. 2 filters may also be used as described in U.S. Pat. No. 7,537,791). The precipitate may be discarded and the resulting serum fraction filtrate can undergo further processing for stabilization. Stabilization of the serum fraction filtrate is achieved by adding preservatives (no exogenous anti-oxidant is required as was previously described in U.S. Pat. No. 7,537,791) and incubating the mixture until complete solubilization is achieved. The preservatives useful for stabilization of the serum fraction filtrate include the following: 0.1% potassium sorbate, 0.1% sodium benzoate, 0.1% sodium methyl paraben, and/or 0.1% citric acid. The recommended storage conditions for the camellia serum fraction includes storage in a closed container protected from light at a temperature of between 15° C. and 25° C.

Similar processing of *chrysanthemum parthenium, petroselinum crispum,* or *macrocystis pyrifera* can yield the serum fractions of feverfew, parsley, or kelp, respectively.

In some embodiments, the skin care composition comprises an effective amount of skin tone agents that comprises a first combination of a camellia serum fraction and a feverfew serum fraction, the camellia serum fraction being present in an amount of from about 0.001 wt % to about 15 wt %, alternatively from about 0.002 wt % to about 10 wt %, alternately from about 0.025 wt % to about 10 wt %, in other embodiments from about 0.05 wt % to about 10 wt %, in others from about 0.05 wt % to about 5 wt %, and in others from about 0.1 wt % to about 5 wt %; and the feverfew serum fraction being present in an amount from about 0.001 wt % to about 15 wt %, from about 0.002 wt % to about 10 wt %, from about 0.025 wt % to about 10 wt %, from about 0.05 wt % to about 10 wt %, from about 0.05 wt % to about 5 wt %, or from about 0.1 wt % to about 5 wt %, wherein the wt % is based on the weight of the skin care composition.

According to another embodiment, weight ratio of the camellia serum fraction to the feverfew serum fraction ranges from about 10:90 to about 90:10, from about 10:90 to about 50:50; from about 80:20 to about 20:80, from about 30:70 to about 70:30, from about 40:60 to about 60:40. For example, the weight ratio of the camellia serum fraction to feverfew serum fraction may be about 90:10, about 80:20, about 70:30, about 60:40, about 50:50, about 40:60, about 30:70, about 20:80, or about 10:90.

In another embodiment, the skin care composition comprises an effective amount of a second combination of skin tone agents that comprises a parsley serum fraction and a kelp serum fraction, the parsley serum fraction being present in an amount from about 0.001 wt % to about 15 wt %, from about 0.002 wt % to about 10 wt %, from about 0.025 wt % to about 10 wt %, from about 0.05 wt % to about 10 wt %, from about 0.05 wt % to about 5 wt %, or from about 0.1 wt % to about 5 wt %; and the kelp serum fraction being present in an amount from about 0.001 wt % to about 15 wt %, from about 0.002 wt % to about 10 wt %, from about 0.025 wt % to about 10 wt %, from about 0.05 wt % to about 10 wt %, from about 0.05 wt % to about 5 wt %, or from about 0.1 wt % to about 5 wt %, wherein the wt % is based on the weight of the skin care composition.

According to another embodiment, weight ratio of the parsley serum fraction to the kelp serum fraction ranges from about 10:90 to about 90:10, from about 10:90 to about 50:50; from about 80:20 to about 20:80, from about 30:70 to about 70:30, from about 40:60 to about 60:40. For example, the weight ratio of the parsley serum fraction to kelp serum fraction may be about 90:10, about 80:20, about 70:30, about 60:40, about 50:50, about 40:60, about 30:70, about 20:80, or about 10:90.

B. Dermatologically Acceptable Carrier

The compositions of the present invention may also comprise a dermatologically acceptable carrier (which may be referred to as "carrier") for the composition. The phrase "dermatologically acceptable carrier", as used herein, means that the carrier is suitable for topical application to the keratinous tissue, has good aesthetic properties, is compatible with the skin tone agents in the composition, and will not cause any unreasonable safety or toxicity concerns. A suitable carrier is selected to yield a desired product form. Furthermore, the solubility or dispersibility of the components may dictate the form and character of the carrier. In one embodiment, the carrier is present at a level of from about 50 wt % to about 99 wt %, about 60 wt % to about 98 wt %, about 70 wt % to about 98 wt %, or, alternatively, from about 80 wt % to about 95 wt %, by weight of the composition. In another embodiment, the carrier is present in the skin care composition at a level of from about 25 wt % to about 50 wt %, which may be diluted upon application with a suitable carrier diluent.

The carrier can be in a wide variety of forms. Non-limiting examples include simple solutions (e.g., aqueous, organic solvent, or oil based), emulsions, and solid forms (e.g., gels, sticks, flowable solids, or amorphous materials). In certain embodiments, the dermatologically acceptable carrier is in the form of an emulsion. Emulsion may be generally classified as having a continuous aqueous phase (e.g., oil-in-water and water-in-oil-in-water) or a continuous oil phase (e.g., water-in-oil and oil-in-water-in-oil). The oil phase of the present invention may comprise silicone oils, non-silicone oils such as hydrocarbon oils, esters, ethers, and the like, and mixtures thereof.

The aqueous phase comprises water, such as demineralized or distilled water, for example. Other acceptable carriers that may be used in the aqueous carrier include, but are not limited to alcohol compounds, such as ethanol. According to one embodiment, the composition comprises alcohol, dipropylene glycol, and/or water.

The skin care compositions have a pH ranging from about 3.0 to about 10, which may be measured by taking a direct pH measurement using a standard hydrogen electrode of the composition at 25° C. Accordingly, the pH of the skin care composition may be within the range from about 6 to about 9, for example.

Emulsions may further comprise an emulsifier. The composition may comprise any suitable percentage of emulsifier to sufficiently emulsify the carrier. Suitable weight ranges include from about 0.1 wt % to about 10 wt % or about 0.2 wt % to about 5 wt % of an emulsifier, based on the weight of the composition. Emulsifiers may be nonionic, anionic or cationic. Suitable emulsifiers are disclosed in, for example, U.S. Pat. No. 3,755,560, U.S. Pat. No. 4,421,769, and *McCutcheon's Detergents and Emulsifiers*, North American Edition, pages 317-324 (1986), which are incorporated herein by reference in their entirety. Suitable emulsions may have a wide range of viscosities, depending on the desired product form.

C. Optional Ingredients

According to embodiments of the present invention, the skin care compositions can also additionally comprise suitable optional ingredients as desired. For example, the composition can optionally include other active or inactive ingredients, provided that they do not unacceptably alter the benefits of the skin care composition. When present, compositions of the present invention may contain from about 0.0001% to about 50%; from about 0.001% to about 20%; or, alternately, from about 0.01% to about 10%, by weight of the composition, of the optional components. The amounts listed herein are only to be used as a guide, as the optimum amount of the optional components used in a composition will depend on the specific active selected since their potency does vary considerably. Hence, the amount of some optional components useful in the present invention may be outside the ranges listed herein.

The optional components, when incorporated into the composition, should be suitable for use in contact with human skin tissue without undue toxicity, incompatibility, instability, allergic response, and the like. The compositions of the present invention may include optional components such as anti-acne actives, desquamation actives, anti-cellulite agents, chelating agents, flavonoids, tanning active, non-vitamin antioxidants and radical scavengers, skin growth regulators, anti-wrinkle actives, anti-atrophy actives, minerals, phytosterols and/or plant hormones, N-acyl amino acid compounds, antimicrobial or antifungal actives, and other useful skin care actives, which are described in further detail in U.S. application publication No. US2006/0275237A1 and US2004/0175347A1.

According to yet another embodiment, the skin care composition may further include one or more additional skin care actives. Accordingly, non-limiting examples of additional skin care actives include flavonoids such as apigenin and luteolin, indole compounds, xanthine compounds, vitamin $B_3$ compounds, panthenol compounds, and derivatives thereof.

1. Flavonoids

The compositions of embodiments of the present invention may optionally contain a flavonoid compound. Flavonoids are broadly disclosed in U.S. Pat. Nos. 5,686,082 and 5,686,367, both of which are herein incorporated by reference. Flavonoids suitable for use in embodiments of the present invention are flavanones selected from unsubstituted flavanones, mono-substituted flavanones, and mixtures thereof; chalcones selected from unsubstituted chalcones, mono-substituted chalcones, di-substituted chalcones, tri-substituted chalcones, and mixtures thereof; flavones selected from unsubstituted flavones, mono-substituted flavones, di-substituted flavones, and mixtures thereof; one or more isoflavones; coumarins selected from unsubstituted coumarins, mono-substituted coumarins, di-substituted coumarins, and mixtures thereof; chromones selected from unsubstituted chromones, mono-substituted chromones, di-substituted chromones, and mixtures thereof; one or more dicoumarols; one or more chromanones; one or more chromanols; isomers (e.g., cis/trans isomers) thereof; and mixtures thereof. By the term "substituted" as used herein means flavonoids wherein one or more hydrogen atom of the flavonoid has been independently replaced with hydroxyl, C1-C8 alkyl, C1-C4 alkoxyl, 0-glycoside, and the like or a mixture of these substituents.

Examples of suitable flavonoids include, but are not limited to, unsubstituted flavanone, mono-hydroxy flavanones (e.g., 2'-hydroxy flavanone, 6-hydroxy flavanone, 7-hydroxy flavanone, etc.), mono-alkoxy flavanones (e.g., 5-methoxy flavanone, 6-methoxy flavanone, 7-methoxy flavanone, 4'-methoxy flavanone, etc.), unsubstituted chalcone (especially unsubstituted trans-chalcone), mono-hydroxy chalcones (e.g., 2'-hydroxy chalcone, 4'-hydroxy chalcone, etc.), di-hydroxy chalcones (e.g., 2',4-dihydroxy chalcone, 2',4'-dihydroxy chalcone, 2,2'-dihydroxy chalcone, 2',3-dihydroxy chalcone, 2',5'-dihydroxy chalcone, etc.), and tri-hydroxy chalcones (e.g., 2',3',4'-trihydroxy chalcone, 4,2',4'-trihydroxy chalcone, 2,2',4'-trihydroxy chalcone, etc.), unsubstituted flavone, 7,2'-dihydroxy flavone, 3',4'-dihydroxy naphthoflavone, 4'-hydroxy flavone, 5,6-benzoflavone, and 7,8-benzoflavone, unsubstituted isoflavone, daidzein (7,4'-dihydroxy iso flavone), 5,7-dihydroxy-4'-methoxy isoflavone, soy isoflavones (a mixture extracted from soy), unsubstituted coumarin, 4-hydroxy coumarin, 7-hydroxy coumarin, 6-hydroxy-4-methyl coumarin, unsubstituted chromone, 3-formyl chromone, 3-formyl-6-isopropyl chromone, unsubstituted dicoumarol, unsubstituted chromanone, unsubstituted chromanol, and mixtures thereof.

In an embodiment, the flavonoid compound is an unsubstituted flavanone, methoxy flavanones, unsubstituted chalcone, 2',4-dihydroxy chalcone, and mixtures thereof. For example, in another embodiment, are unsubstituted flavanone, unsubstituted chalcone (e.g., the trans isomer), and mixtures thereof.

Flavonoids can be synthetic materials or obtained as extracts from natural sources (e.g., plants). The naturally sourced material can also further be derivatized (e.g., an ester or ether derivative prepared following extraction from a natural source). Flavonoid compounds useful herein are commercially available from a number of sources, e.g., Indofine Chemical Company, Inc. (Somerville, N.J.), Steraloids, Inc. (Wilton, N.H.), and Aldrich Chemical Company, Inc. (Milwaukee, Wis.).

Mixtures of the above flavonoid compounds may also be used.

When included in the skin care composition, the herein described flavonoid compounds can be present at concentrations of from about 0.01 wt % to about 20 wt %, of from about 0.1 wt % to about 10 wt %, or from about 0.5 wt % to about 5 wt %, wherein the wt % is based on the total weight of the skin care composition.

2. Indole Compounds

The skin care compositions can further include an indole compound. As used herein, "indole compound" means one or more indoles, derivatives thereof, mixtures thereof, or salts thereof. Accordingly, the composition may include from about 0.1 wt % to about 10 wt % of the indole compound, from about 0.5 wt % to about 5 wt % of the indole compound, or from about 1 wt % to about 2 wt % of the indole compound, for example, wherein the wt % is based on the total weight of the skin care composition.

3. Xanthine Compounds

The skin care compositions can further include a xanthine compound. As used herein, "xanthine compound" means one or more xanthines, derivatives thereof, and mixtures thereof. Xanthine compounds that can be useful herein include, but are not limited to, caffeine, xanthine, 1-methylxanthine, theophylline, theobromine, derivatives thereof, and mixtures thereof. Accordingly, the composition may include from about 0.1 wt % to about 10 wt % of the xanthine compound, from about 0.5 wt % to about 5 wt % of the xanthine compound, or from about 1 wt % to about 2 wt % of the xanthine compound, for example, wherein the wt % is based on the total weight of the skin care composition. For example, the skin care composition may further include about 0.75 wt % of caffeine.

4. Vitamin $B_3$ Compounds

The skin care compositions can further include a vitamin $B_3$ compound. As used herein, "vitamin $B_3$ compound" means nicotinic acid, niacinamide, nicotinyl alcohol, derivatives thereof, and mixtures thereof. The vitamin $B_3$ compound may be included as the substantially pure material, or as an extract obtained by suitable physical and/or chemical isolation from natural (e.g., plant) sources. Accordingly, the composition may include from about 0.1 wt % to about 25 wt % of the vitamin $B_3$ compound; from about 0.5 wt % to about 15 wt % of the vitamin $B_3$ compound; or from about 3.5 wt % to about 7.5 wt % of the vitamin $B_3$ compound, for example, wherein the wt % is based on the total weight of the skin care composition. For example, the skin care composition may further include about 2.5 wt % of vitamin $B_3$.

5. Panthenol Compounds

The skin care compositions can further comprise a panthenol compound. As used herein, the term "panthenol compound" includes panthenol, one or more pantothenic acid derivatives, and mixtures thereof. Non-limiting examples of panthenol compounds include D-panthenol ([R]-2,4-dihydroxy-N-[3-hydroxypropyl]-3,3-dimethylbutamide), D,L-panthenol, pantothenic acids and their salts (e.g., the calcium salt), panthenyl triacetate, royal jelly, panthetine, pantotheine, panthenyl ethyl ether, pangamic acid, pantoyl lactose, Vitamin B complex, or mixtures thereof. Accordingly, the composition may include from about 0.01 wt % to about 5 wt % of the panthenol compound; from about 0.03 wt % to about 3 wt % of the panthenol compound; from about 0.05 wt % to about 2 wt % of the panthenol compound; or from about 0.1 wt % to about 1 wt % of the panthenol compound, for example, wherein the wt % is based on the total weight of the skin care composition. For example, the skin care composition may further include about 0.15 wt % of panthenol.

6. Additional Skin Tone Agent

In some embodiments, it may be desirable to include one or more additional skin tone agents in the composition. The additional skin tone agents can be included to further improve overall skin tone. When present, the compositions of the present invention contain up to about 50%, 40%, 30%, 20%, 10%, 5%, or 3%, by weight of the composition, of the skin tone agent. When present, the compositions of the present invention contain at least about 0.001%, 0.01%, 0.1%, 0.2%, 0.5%, or 1%, by weight of the composition, of the additional skin tone agent. Suitable ranges include any combination of the lower and upper limits including suitable ranges from about 0.1% to about 50%; from about 0.2% to about 20%; or from about 1% to about 10%, by weight of the composition, of the skin tone agent. The amounts listed herein are only to be used as a guide, as the optimum amount of the skin tone agent will depend on the specific active selected since their potency does vary considerably.

Suitable additional skin tone agents include, but are not limited to, sugar amines, vitamin B3 compounds, arbutin, deoxyarbutin, 1,3-dihydroxy-4-alkylbenzene such as hexylresorcinol, sucrose dilaurante, bakuchoil (4-[(1E,3S)-3-ethenyl-3,7-dimethyl-1,6 octadienyl]phenol or monterpene phenol), pyrenoine (available from Biotech Marine, France), *panicum miliaceum* seed extract, arlatone dioic acid, cinnamic acid, ferulic acid, achromaxyl, methyl nicotinamide, oil soluble licorice extract, folic acid, undecylenic acid (i.e., undecenoic acid), zinc undecylenate, thiamine (Vitamin B1) and its hydrochloride, L-tryptophan, *helianthus annuus* (sunflower) and *vitis vinifera* (grape) leaf extract, carnosine (i.e., dragosine), methyl gentisate, 1,2-hexandiol and 1,2-octandiol (i.e., combination sold as Symdiol 68 by Symrise AG, Germany), inositol, decylenoylphenylalanine (e.g., sold under the tradename Sepiwhite by Seppic, France), koijic acid, hexamidine compounds, salicylic acid, and retinoids including retinol and retinol propionate.

In certain embodiments, the additional skin tone agent is selected from vitamin B3 compounds, sugar amines, hexamidine compounds, salicylic acid, 1,3-dihydroxy-4-alkylbenzene such as hexylresorcinol, and retinoids. As used herein, "vitamin $B_3$ compound" means a compound having the formula:

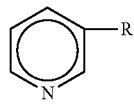

wherein R is —$CONH_2$ (i.e., niacinamide), —COOH (i.e., nicotinic acid) or —$CH_2OH$ (i.e., nicotinyl alcohol); derivatives thereof; and salts of any of the foregoing. As used herein, "sugar amine" includes isomers and tautomers of such and its salts (e.g., HCl salt) and its derivatives. Examples of sugar amines include glucosamine, N-acetyl glucosamine, mannosamine, N-acetyl mannosamine, galactosamine, N-acetyl galactosamine, their isomers (e.g., stereoisomers), and their salts (e.g., HCl salt). As used herein, "hexaminide compound" means a compound having the formula:

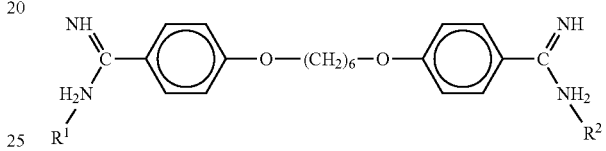

wherein $R^1$ and $R^2$ are optional or are organic acids (e.g., sulfonic acids, etc.). In one embodiment, hexamidine compound is hexamidine diisethionate.

7. Additional Anti-Inflammatory Agents Hypopigmentation may result from skin inflammation. Transient inflammatory events triggering hypopigmentation and, more specifically, post-inflammatory hypopigmentation include, but are not limited to, acne lesions, ingrown skins, scratches, insect bites, surfactant damage, allergens, and short-term UV exposure. Inflammation induced hypopigmentation including post-inflammatory hypopigmentation may be managed by the skin care compositions provide herein, insofar as the blend of the camellia serum fraction and the feverfew serum fraction, and the blend of the kelp serum fraction and the parsley serum fraction inhibit inflammation, as indicated by the inhibition of interleukin-1 receptor-associated kinase (IRAK-4). However, by incorporating into the compositions of the present invention an additional anti-inflammatory agent, enhanced or synergistic benefits may be achieved. When present, the compositions of the present invention contain up to about 20%, 10%, 5%, 3%, or 1% by weight of the composition, of the additional anti-inflammatory agent. When present, the compositions of the embodiments of the present invention contain at least about 0.001%, 0.01%, 0.1%, 0.2%, 0.3%, 0.5%, or 1%, by weight of the composition, of the additional anti-inflammatory agent. Suitable ranges include any combination of the lower and upper limits. Suitable additional anti-inflammatory agents include, but are not limited to nonsteroidal anti-inflammatory agents (NSAIDS including but not limited to ibuprofen, naproxen, flufenamic acid, etofenamate, aspirin, mefenamic acid, meclofenamic acid, piroxicam and felbinac), glycyrrhizic acid (also known as glycyrrhizin, glycyrrhixinic acid, and glycyrrhetinic acid glycoside) and salts such as dipotassium glycyrrhizate, glycyrrhetenic acid, licorice extracts, bisabolol (e.g., alpha bisabolol), manjistha (extracted from plants in the genus *Rubia*, particularly *Rubia cordifolia*), and guggal (extracted from plants in the genus *Commiphora*, particularly *Commiphora mukul*), kola extract, chamomile, red clover extract, and sea whip extract (extracts from plant in the order *Gorgonacea*), derivatives of any of the foregoing, and mixtures thereof.

8. Sunscreen Actives

The compositions of the subject invention may comprise one or more sunscreen actives (or sunscreen agents) and/or ultraviolet light absorbers. Herein, "sunscreen active" collectively includes, sunscreen actives, sunscreen agents, and/or ultraviolet light absorbers. Sunscreen actives include both sunscreen agents and physical sunblocks. Sunscreen actives may be organic or inorganic. Examples of suitable sunscreen actives are disclosed in Personal Care Product Council's *International Cosmetic Ingredient Dictionary and Handbook*, Thirteenth Edition, as "sunscreen agents." Particularly suitable sunscreen actives are 2-ethylhexyl-p-methoxycinnamate (commercially available as PARSOL™ MCX), 4,4'-t-butyl methoxydibenzoyl-methane (commercially available as PARSOL™ 1789), 2-hydroxy-4-methoxybenzophenone, octyldimethyl-p-aminobenzoic acid, digalloyltrioleate, 2,2-dihydroxy-4-methoxybenzophenone, ethyl-4-(bis(hydroxypropyl))aminobenzoate, 2-ethylhexyl-2-cyano-3,3-diphenylacrylate, 2-ethylhexyl-salicylate, glyceryl-p-aminobenzoate, 3,3,5-tri-methylcyclohexylsalicylate, menthyl anthranilate, p-dimethyl-aminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonicbenzoxazoic acid, octocrylene, zinc oxide, benzylidene camphor and derivatives thereof, titanium dioxide, and mixtures thereof.

In one embodiment, the composition may comprise from about 1% to about 20%, and alternatively from about 2% to about 10% by weight of the composition, of the sunscreen active. Exact amounts will vary depending upon the chosen sunscreen active and the desired Sun Protection Factor (SPF), which is within the knowledge of one of skilled in the art.

II. Methods of Treatment

Various methods of treatment, application, regulation, or improvement may utilize the aforementioned compositions. In one embodiment, the method includes the step of identifying a hypopigmented spot for improvement by the composition. The hypopigmented spot may be identified by the user or a third party such as a dermatologist, cosmetician, or other caregiver. Identification may be done by visual inspection of the skin for hypopigmented spots in need of treatment based on size and/or color. Identification may also be done by commercially available imaging devices such SIAscope® V (available from Astron Clinica, Ltd., UK) or the VISIA® Complexion Analysis system (available from Canfield Scientific, Inc., Fairfield, N.J.). Both devices are capable of collecting images of the skin and identifying hypopigmented spots. In some instances, the method comprises the step of identifying a plurality of hypopigmented spots for treatment by the composition.

Identification of the hypopigmented spot may occur on any skin surface of the body. Skin surfaces of the most concern tend to be those not typically covered by clothing such as facial skin surfaces, hand and arm skin surfaces, foot and leg skin surfaces, and neck and chest skin surfaces. In particular, identification of the hypopigmented spot may be on a facial skin surface including the forehead, perioral, chin, periorbital, nose, and/or cheek skin surfaces.

The method may comprise the step of applying the composition to a hypopigmented spot or spots, which may have been previously identified. Many regimens exist for the application of the composition to the hypopigmented spot. The composition may be applied at least once a day, twice a day, or on a more frequent daily basis, during a treatment period. When applied twice daily, the first and second applications are separated by at least 1 to about 12 hours. Typically, the composition may be applied in the morning and/or in the evening before bed.

The treatment period is ideally of sufficient time to provide an improvement in the hypopigmented spot. The improvement may be a detectable reduction in size of the hypopigmented spot, darkening of the hypopigmented spot, increase in melanin of the hypopigmented spot, or evening of the tone of skin. The treatment period may be at least about 1 week. The treatment period may last about 4 weeks or about 8 weeks. In certain embodiments, the treatment period will extend over multiple months (i.e., 3-12 months) or multiple years. In one embodiment the composition is applied to the hypopigmented spot(s) at least once a day during a treatment period of at least about 4 weeks or at least about 8 weeks. In one embodiment the composition is applied to the hypopigmented spot(s) twice a day during a treatment period of at least about 4 weeks or 8 weeks.

In still another embodiment, the method comprises applying the skin care composition according to a regimen, wherein said regimen comprises:

(a) cleansing the skin to form a cleansed skin surface;
(b) topically applying the skin care composition to said cleansed skin surface.

The skin care composition may be used daily, weekly, or in a variety of regimens. The skin care composition may be used more than once a day, such as at night and in the morning. The skin care composition may be used more than once per day on certain days or use only a few times per week. The skin care composition may be used three times per day, twice per day, once per day, six times per week, five times per week, four times per week, three times per week, two times per week, or one time per week. In some embodiments, the skin care composition is used four, five, six or seven times per week.

The step of applying the composition to the hypopigmented spot may be accomplished by localized application. In reference to application of the composition, the term "localized", "local", or "locally" mean that the composition is delivered the targeted area (such as the hypopigmented spot) while minimizing delivery to skin surface not requiring treatment. The composition may be applied and lightly massaged into the hypopigmented spot. It is recognized that localized application does allow for a reasonable amount of the composition to be applied to areas adjacent the hypopigmented spot (i.e., the composition is unlikely to be applied or to remain within the boundary of the hypopigmented spot without some spreading). The form of the composition or the dermatologically acceptable carrier should be selected to facilitate localized application. While certain embodiments of the present invention contemplate applying a composition locally to a hypopigmented spot, it will be appreciated that compositions of the present invention can be applied more generally or broadly to one or more facial skin surfaces to reduce the appearance of hypopigmented spots within those facial skin regions.

In some embodiments, the composition may be delivered by a variety of applicators appropriate for localized and general application. Such applicators can include droppers, applicator wands, cotton swabs, or any other suitable device. Other suitable applicators include SH-0127 pen applicator available from Shya Hsin Plastic Works, Inc., Taiwan and either the Xpress Tip or liquid filled swab available from SwabPlus, Inc., China. The applicator may be configured to easily apply the composition to hypopigmented spots having an approximate diameter between about 2 mm and about 10 mm and allowing for a dosed amount of the composition of between about 1 to about 50 μL/cm$^2$ or between about 1 to about 5 μL/cm$^2$. In another embodiment, the composition is applied to the one or more hypopigmented spots and more generally to one or more facial skin surfaces contemporaneously (i.e., over a period of less than 30 minutes or, more typically, less than 5 minutes).

While some methods described herein contemplate applying the compositions of the present invention with an applicator, it will be appreciated that applicators are not required and the compositions of the present invention can also be applied directly by using one's finger or in other conventional manners.

In one embodiment, the method comprises the steps of applying a first composition comprising an effective amount of a blend of a camellia serum fraction and a feverfew serum fraction to a hypopigmented spot or a plurality of hypopigmented spots on a skin surface. In another embodiment, the method comprises the steps of applying a first composition comprising an effective amount of a blend of a kelp serum fraction and a parsley serum fraction to a hypopigmented spot or a plurality of hypopigmented spots on a skin surface. In another embodiment, the method comprises the steps of applying a first composition comprising an effective amount of a combination of a blend of a camellia serum fraction and a feverfew serum fraction, and a blend of a kelp serum fraction and a parsley serum fraction to a hypopigmented spot or a plurality of hypopigmented spots on a skin surface. Accordingly, the first composition may be any compositions described herein.

In another embodiment, the method further comprises applying a second composition, which may optionally comprise an effective amount of the serum fraction blends present in the first composition. The first and/or the second compositions may comprise one or more tone agents, sunscreen actives, anti-inflammatory agents, or optional components. The first composition may be locally applied to the hypopigmented spot or plurality of hypopigmented spots. The second composition may be locally applied to the hypopigmented spot or a plurality of hypopigmented spots to which the first composition is applied or the second composition may be applied more generally to the skin surface including the hypopigmented spots to which the first composition is applied. In certain embodiments, the skin surface is facial skin surface which include one or more of the forehead, perioral, chin, periorbital, nose, and cheek skin surfaces. In another embodiment, the first and second compositions are applied contemporaneously to at least the cheek, forehead, and chin/perioral skin surfaces. For general application to a skin surface and, particularly a facial skin surface, the dosed amount of the first or second composition may be between about 1 to about 50 μL/cm$^2$ per application (i.e., per single application to the skin surfaces).

Suitable methods may comprise any one or more of the abovementioned steps. All of the aforementioned steps are applicable to application, treatment, regulation, and/or improvement of both a single hypopigmented spot as well as a plurality of hypopigmented spots. Likewise, the exemplary methods that follow are applicable to both a single hypopigmented spot as well as a plurality of hypopigmented spots.

One suitable method of improving the appearance of a hypopigmented spot includes the step of topically applying a composition comprising an effective amount of a blend of a camellia serum fraction and a feverfew serum fraction, and/or a blend of a kelp serum fraction and a parsley serum fraction to the hypopigmented spot on a skin surface, wherein the composition is applied for a period of time sufficient for the serum fractions to improve the appearance of the hypopigmented spot. Another suitable method of improving the appearance of hypopigmented spots includes the steps of identifying a hypopigmented spot on a skin surface, applying a composition comprising an effective amount of the serum fraction blend to the hypopigmented spot on the skin surface, wherein the composition is applied for a period of time sufficient for the serum fractions to improve the appearance of the hypopigmented spot.

Another suitable method is for improving the appearance of a post-inflammatory hypopigmentation. The method may comprise the steps of identifying an area of post-inflammatory hypopigmentation on a skin surface and of applying to the area said skin care composition comprising a blend of the serum fractions, which also provides anti-inflammatory effect. An effective amount of said serum fractions may be applied at least daily for a period of time sufficient to improve the appearance of the area of post-inflammatory hypopigmentation. The compositions may further comprise a sunscreen active, an additional skin tone agent, or combinations thereof.

FORMULATIONS AND EXAMPLES

The following are non-limiting examples of the present invention. The examples are given solely for the purpose of illustration and are not to be construed as limitations of the present invention, as many variations thereof are possible without departing from the spirit and scope of the invention, which would be recognized by one of ordinary skill in the art.

In the examples, all concentrations are listed as weight percent, unless otherwise specified and may exclude minor materials such as diluents, filler, and so forth. The listed formulations, therefore, comprise the listed components and any minor materials associated with such components. As is apparent to one of ordinary skill in the art, the selection of these minors will vary depending on the physical and chemical characteristics of the particular ingredients selected to make the present invention as described herein.

Exemplary Compositions

Table 1 sets forth non-limiting examples of the compositions of the present invention. The examples are given solely for the purpose of illustration and are not to be construed as limitations of the present invention, as many variations thereof are possible without departing from the spirit and scope of the invention, which would be recognized by one of ordinary skill in the art. In the examples, all concentrations are listed as weight percent, unless otherwise specified and may exclude minor materials such as diluents, filler, and so forth. The listed formulations, therefore, comprise the listed components and any minor materials associated with such components. As is apparent to one of ordinary skill in the art, the selection of these minor materials will vary depending on the physical and chemical characteristics of the particular ingredients selected to make the present invention as described herein.

All examples may be used to treat or improve the appearance of one or more hypopigmented spots. The present invention may further relate to a regimen involving the localized treatment for one or more hypopigmented spots by a first composition and/or a more broad or general facial skin treatment by a second composition, which can be applied before or after the localized treatment to improve skin tone across the face.

TABLE 1

TABLE 1: Exemplary Compositions

| Component/% by wt. | Ex. A | Ex. B | Ex. C | Ex. D | Ex. E | Ex. F |
|---|---|---|---|---|---|---|
| *camellia sinensis* (*camellia* serum fraction) (manufactured by IBT*) | 1 | 0.4 | 1.6 | — | — | — |
| *chrysanthemum parthenium* (feverfew serum fraction) (manufactured by IBT*) | 1 | 1.6 | 0.4 | — | — | — |
| *petroselinum crispum* (parsley serum fraction) (manufactured by IBT*) | — | — | — | 1 | 0.4 | 1.6 |
| *macrocystis pyrifera* (kelp serum fraction) (manufactured by IBT) | — | — | — | 1 | 1.6 | 0.4 |
| N-Acetylglucosamine | 0.00 | 2.00 | 0.00 | 0.00 | 2.00 | 0.00 |
| Hexamidine Diisethionate | 0.00 | 0.09 | 0.09 | 0.00 | 0.09 | 0.09 |
| Sepiwhite ™ (Undecylenoyl-phenylalanine, neutralized) (available from SEPPIC) | 0.00 | 0.50 | 0.50 | 0.00 | 0.50 | 0.50 |
| Sepigel 305 ™ (Polyacrylamide + C13-14 isoparaffin + laureth-7) (available from SEPPIC) | 0.00 | 2.00 | 2.00 | 0.00 | 2.00 | 2.00 |
| Dipotassium Glycyrrhizate | 0.00 | 0.10 | 0.30 | 0.00 | 0.10 | 0.30 |
| Hexamidine Diisethionate | 0.00 | 0.09 | 0.09 | 0.00 | 0.09 | 0.09 |
| Homosalate | 0.00 | 0.00 | 9.00 | 0.00 | 0.00 | 9.00 |
| Avobenzone | 0.00 | 0.00 | 3.00 | 0.00 | 0.00 | 3.00 |
| Octocrylene | 0.00 | 0.00 | 2.60 | 0.00 | 0.00 | 2.60 |
| Oxybenzone | 0.00 | 0.00 | 1.00 | 0.00 | 0.00 | 1.00 |
| Octisalate | 0.00 | 0.00 | 4.50 | 0.00 | 0.00 | 4.50 |
| Butylene Glycol (CAS No. 107-88-0) | 5.50 | 5.50 | 5.50 | 5.50 | 5.50 | 5.50 |
| Niacinamide (CAS No. 98-92-0) | 5.00 | 5.00 | 5.00 | 5.00 | 5.00 | 5.00 |
| Glycerin (CAS No. 56-81-5) | 2.50 | 2.50 | 2.50 | 2.50 | 2.50 | 2.50 |
| DC 1503 Fluid ™ (available from DowCorning) | 2.50 | 2.50 | 2.50 | 2.50 | 2.50 | 2.50 |
| Lubrajel Oil ™(available from Sederma) | 1.44 | 1.44 | 1.44 | 1.44 | 1.44 | 1.44 |
| Phenonip XB ™ (available from Clariant) | 1.25 | 1.25 | 1.25 | 1.25 | 1.25 | 1.25 |
| D-panthenol (CAS No. 81-13-0) | 1.00 | 1.00 | 1.00 | 1.00 | 1.00 | 1.00 |
| Tospearl 2000 ™ (Polymethylsilsesquioxane) (CAS No. 68554-70-1) (available from GE Silicones/Momentive) | 1.00 | 1.00 | 1.00 | 1.00 | 1.00 | 1.00 |
| DL-Alpha Tocopheryl Acetate (CAS No. 7695-91-2) | 0.50 | 0.50 | 0.50 | 0.50 | 0.50 | 0.50 |
| Prodew 400 ™ (available from Ajinomoto) | 0.50 | 0.50 | 0.50 | 0.50 | 0.50 | 0.50 |
| Pemulen TR-2 ™ (Acrylates/C10-30 Alkyl Acrylate Crosspolymer) (available from Noveon) | 0.25 | 0.25 | 0.25 | 0.25 | 0.25 | 0.25 |
| Polysorbate 20 (CAS No. 9005-64-5) | 0.25 | 0.25 | 0.25 | 0.25 | 0.25 | 0.25 |
| Sodium Metabisulfite (CAS No. 7681-57-4) | 0.25 | 0.25 | 0.25 | 0.25 | 0.25 | 0.25 |
| Allantoin (CAS No. 97-59-6) | 0.20 | 0.20 | 0.20 | 0.20 | 0.20 | 0.20 |
| Sodium Hydroxide (CAS No. 1310-73-2) (50% solution by weight in water) | 0.17 | 0.17 | 0.17 | 0.17 | 0.17 | 0.17 |

TABLE 1-continued

TABLE 1: Exemplary Compositions

| Component/% by wt. | Ex. A | Ex. B | Ex. C | Ex. D | Ex. E | Ex. F |
|---|---|---|---|---|---|---|
| Disodium EDTA (CAS No. 139-33-3) | 0.10 | 0.10 | 0.10 | 0.10 | 0.10 | 0.10 |
| Xanthan Gum (CAS No. 11138-66-2) | 0.05 | 0.05 | 0.05 | 0.05 | 0.05 | 0.05 |
| Sodium Hyaluronate (CAS No. 9067-32-7) | 0.01 | 0.01 | 0.01 | 0.01 | 0.01 | 0.01 |
| Water (CAS No. 7732-18-5) | QS | QS | QS | QS | QS | QS |
| TOTAL (% by weight of total composition) | 100.00 | 100.00 | 100.00 | 100.00 | 100.00 | 100.00 |

*IBT is an abbreviation for Integrated Botanical Technologies, which is now Akzo Nobel Surface Chemistry LLC, Chicago, Illinois.

According to embodiments of the present invention, the skin care compositions are generally prepared by conventional methods such as are known in the art of making topical compositions. Such methods typically involve mixing of the ingredients in one or more steps to a relatively uniform state, with or without heating, cooling, application of vacuum, and the like. Typically, emulsions are prepared by first mixing the aqueous phase materials separately from the fatty phase materials and then combining the two phases as appropriate to yield the desired continuous phase. The compositions are preferably prepared such as to optimize stability (physical stability, chemical stability, photostability) and/or delivery of the active materials. This optimization may include appropriate pH (e.g., less than 7), exclusion of materials that can complex with the active agent and thus negatively impact stability or delivery (e.g., exclusion of contaminating iron), use of approaches to prevent complex formation (e.g., appropriate dispersing agents or dual compartment packaging), use of appropriate photostability approaches (e.g., incorporation of sunscreen/sunblock, use of opaque packaging), etc.

III. Bio-Activity

Although not wishing to be limited by theory, it is believed that topical application of various skin tone agents can: (1) stimulate the production of melanin in skin melanocytes; and/or (2) interrupt or inhibit an inflammatory cycle. Furthermore, the topical application can lead to evenly toned skin and afford the appearance of younger looking skin.

One method for predicting the efficacy of the blends of serum fractions to affect the inflammatory cycle is using in vitro bio-assays. More specifically, interleukin signaling inhibition via interleukin-1 receptor-associated kinase (IRAK-4) inhibition is the predictive bioassay method described below.

Interleukin-1 Signaling Inhibition: Interleukin-1 (IL-1) is a family of pro-inflammatory cytokines that initiate biochemical signaling pathways to increase inflammation. In the skin, IL-1 is an endogenous factor that induces an inflammatory action. It is believed that inhibition of IL-1 signaling at any point within its pathways inhibits inflammation.

Interleukin-1 receptor-associated kinase inhibition: Interleukin-1 receptor-associated kinase (IRAK-4) is an integral mediator of IL-1 signaling that recruits other kinases upon IL-1 stimulation for subsequent signal transduction. The inhibition of IRAK-4 activity is measured by the amount of ATP using the ADP-Glo™ kinase kit (Promega) after incubation of the full-length human recombinant IRAK-4 enzyme system (Promega) with inhibitors for 30 minutes. The ADP-Glo™ kit was used in accordance with the manufacturer's instructions.

Melanin synthesis activation: Melanin is the pigment made by melanocytes that is responsible for skin color. Melanin synthesis only occurs during the anagen phase. Prolonging the anagen phase potentially prolongs melanin synthesis and also provides the opportunity to increase the synthesis of melanin with specific activators. The activation of melanin is measured in an in vitro model of B16-F1 melanocytes (ATCC) in culture. Melanocytes are incubated with activators for 48 hours and the melanin formed is measured by reading the optical density (O.D.) at 410 nm on a spectrophotometer.

Melanin Synthesis Activation Materials: Plates: Corning® 96 Well Flat Clear Bottom White Polystyrene TC-Treated Microplates, #3903; Cells: B16-F1 (ATCC); Growing Medium: DMEM, Gibco Invitrogen, #11965-092 with 10% FBS and 1% Penicillin/strep/Glutamine (GLBCO cat#15701); serum fractions and blends; preservatives; and controls.

Melanin Synthesis Activation Method: Day 1: Seeding B16-F1 cells, 2000/well/100 ul; Day 2: Treating the compounds by adding 10 µl of diluted compounds into each well; and Day 4: Measure the color change in each well. Checking the cell viability under microscope, if cell confluence is <50%, the data for this point is not used. Measuring OD value (melanin product) at Vis/UV reader, 410 nM after adding 100 µl of 1% NaOH (1 ml 50% NaOH+49 ml H2O) into each well. Note: Due to prevalence of color with serum fractions, wells with media but no cells were also treated and used as color control blanks to remove over-estimation due to serum color.

Statistical Significance Definition: One-tailed 2-sample t-tests were conducted. Statistical significance is defined as $p<0.05$. Examples in this application are provided with values of $p<0.01$. Statistically significant and synergistic blends are defined as blends with statistically significantly greater activity than that of both individual serum fraction components.

A. Kelp and Parsley Serum Fractions (1) The kelp serum fraction, the parsley fraction, and combinations can be assessed for melanin synthesis action (all serum fractions analyzed at 1% (v/v) of the analytical composition):

TABLE 1

Example 1A: Kelp-Parsley 10:90 Blend
K: Lot# MP0726M/MS-0571; P: Lot #PA1117L/HP-0570;
K + P: Lot #: B19-0729M/OS-0572

| Serum Fraction (1%) | Fold activation | 2-sample t-test vs. blend ($p < 0.01$ statistically significant) |
|---|---|---|
| Kelp | 1.62 | 0.000008 |
| Parsley | 1.91 | 0.000010 |
| Kelp-Parsley 10:90 Blend | 6.36 | |

TABLE 2

Example 1B: Kelp-Parsley 20:80 Blend
K: Lot# MP0726M/MS-0571; P: Lot #PA1117L/HP-0570;
K + P: Lot #: B19-0729M/OS-0573

| Serum Fraction (1%) | Fold activation | 2-sample t-test vs. blend ($p < 0.01$ statistically significant) |
|---|---|---|
| Kelp | 1.62 | 0.000016 |
| Parsley | 1.91 | 0.000022 |
| Kelp-Parsley 20:80 Blend | 4.25 | |

TABLE 3

Example 1C: Kelp-Parsley 30:70 Blend
K: Lot# MP0726M/MS-0571; P: Lot #PA1117L/HP-0570;
K + P: Lot #: B19-0729M/OS-0574

| Serum Fraction (1%) | Fold activation | 2-sample t-test vs. blend ($p < 0.01$ statistically significant) |
|---|---|---|
| Kelp | 1.62 | 0.001324 |
| Parsley | 1.91 | 0.004537 |
| Kelp-Parsley 30:70 Blend | 2.66 | |

TABLE 4

Example 1D: Kelp-Parsley 40:60 Blend
K: Lot# MP0726M/MS-0571; P: Lot #PA1117L/HP-0570;
K + P: Lot #: B19-0729M/OS-0575

| Serum Fraction (1%) | Fold activation | 2-sample t-test vs. blend ($p < 0.01$ statistically significant) |
|---|---|---|
| Kelp | 1.62 | 0.000004 |
| Parsley | 1.91 | 0.000005 |
| Kelp-Parsley 40:60 Blend | 4.37 | |

TABLE 5

Example 1E: Kelp-Parsley 50:50 Blend
K: Lot# MP0726M/MS-0571; P: Lot #PA1117L/HP-0570;
K + P: Lot #: B19-0729M/OS-0576

| Serum Fraction (1%) | Fold activation | 2-sample t-test vs. blend ($p < 0.01$ statistically significant) |
|---|---|---|
| Kelp | 1.62 | 0.000571 |
| Parsley | 1.91 | 0.001749 |
| Kelp-Parsley 50:50 Blend | 2.77 | |

TABLE 6

Example 1F: Kelp-Parsley 70:30 Blend
K: Lot# MP0726M/MS-0571; P: Lot #PA1117L/HP-0570;
K + P: Lot #: B19-0729M/OS-0578

| Serum Fraction (1%) | Fold activation | 2-sample t-test vs. blend ($p < 0.01$ statistically significant) |
|---|---|---|
| Kelp | 1.62 | 0.001198 |
| Parsley | 1.91 | 0.004543 |
| Kelp-Parsley 70:30 Blend | 2.61 | |

TABLE 7

Example 1G: Kelp-Parsley 50:50 Blend
K: Lot# 0320J/MS-0363; P: Lot #PA1117L/HP-0499;
K + P: Lot #: B19-0215M/OS-0529

| Serum Fraction (1%) | Fold activation | 2-sample t-test vs. blend ($p < 0.01$ statistically significant) |
|---|---|---|
| Kelp | 2.13 | 0.000007 |
| Parsley | 1.41 | 0.000007 |
| Kelp-Parsley 50:50 Blend | 6.7 | |

A constant concentration is used to directly demonstrate that the same level of the dry matter content of the blended serum fraction has significantly more activity than the level of either of the individual serum fractions alone. This demonstrates that the two serums in the blend work synergistically together to afford significantly better biological activity. For example in Table 1A, the individual serum fractions of kelp and parsley at 1% give % give 1.62 and 1.91 fold activation but 1% of a 10:90 blend of these individual serum fractions give a significantly and much greater activation of 6.36 fold.

(2) The combination of kelp serum fraction and the parsley serum fraction can be assessed for IRAK-4 inhibition (all serum fractions analyzed at 4% (v/v) of the analytical composition):

TABLE 8

Example 1H: Kelp-Parsley 50:50 Blend
K: Lot# MP0726M/MS-0571; P: Lot #PA1117L/HP-0570;
K + P: Lot #: B19-0729M/OS-0576

| Serum Fraction (4%) | % inhibition | 2-sample t-test vs. blend ($p < 0.01$ statistically significant) |
|---|---|---|
| Kelp | 67.7 | 0.001127 |
| Parsley | 43 | 0.000034 |
| Kelp-Parsley 50:50 Blend | 76.3 | |

TABLE 9

Example 1I: Kelp-Parsley 60:40 Blend
K: Lot# MP0726M/MS-0571; P: Lot #PA1117L/HP-0570;
K + P: Lot #: B19-0729M/OS-0577

| Serum Fraction (4%) | % inhibition | 2-sample t-test vs. blend ($p < 0.01$ statistically significant) |
|---|---|---|
| Kelp | 67.7 | 0.000015 |
| Parsley | 43 | 0.000012 |
| Kelp-Parsley 60:40 Blend | 77.7 | |

TABLE 10

Example 1J: Kelp-Parsley 70:30 Blend
K: Lot# MP0726M/MS-0571; P: Lot #PA1117L/HP-0570;
K + P: Lot #: B19-0729M/OS-0578

| Serum Fraction (4%) | % inhibition | 2-sample t-test vs. blend (p < 0.01 statistically significant) |
|---|---|---|
| Kelp | 67.7 | 0.000336 |
| Parsley | 43 | 0.000022 |
| Kelp-Parsley 70:30 Blend | 76.7 | |

TABLE 11

Example 1K: Kelp-Parsley 80:20 Blend
K: Lot# MP0726M/MS-0571; P: Lot #PA1117L/HP-0570;
K + P: Lot #: B19-0729M/OS-0579

| Serum Fraction (4%) | % inhibition | 2-sample t-test vs. blend (p < 0.01 statistically significant) |
|---|---|---|
| Kelp | 67.7 | 0.001445 |
| Parsley | 43 | 0.000030 |
| Kelp-Parsley 80:20 Blend | 72 | |

A constant concentration was used to directly demonstrate that the same level of dry weight matter in the blended serum fraction has significantly more activity than the level of either of the individual serum fractions alone. This shows that the two serums in the blend work synergistically together to afford significantly better biological activity. For example in Table 11, Experiment 1K, the individual serum fractions of kelp and parsley at 4.0% give 67.7% and 43% inhibition respectively, whereas 4.0% of a 50:50 blend of these serum fractions gives a significantly greater inhibition of 76.3%.

B. Camellia and Feverfew Serum Fractions (1) The camellia serum fraction, the feverfew fraction, and combinations can be assessed for melanin synthesis action (all serum fractions analyzed at 0.8% (v/v) of the analytical composition):

TABLE 12

Example 2A: Camellia-Feverfew 50:50 Blend
C: Lot#TECJ062904-0161-01; F: Lot#FF0811K/TL;
C + F: Lot#B02-0712M/OS-0561

| Serum Fraction (1%) | Fold activation | 2-sample t-test vs. blend (p < 0.01 statistically significant) |
|---|---|---|
| Camellia | 2.26 | 0.003412 |
| Feverfew | 1.72 | 0.000648 |
| Camellia-Feverfew 50:50 Blend | 3.24 | |

TABLE 13

Example 2B: Camellia-Feverfew 80:20 Blend
C: Lot#TECJ062904-0161-01; F: Lot#FF0811K/TL;
C + F: Lot#B02-0719M/OS-0567

| Serum Fraction (1%) | Fold activation | 2-sample t-test vs. blend (p < 0.01 statistically significant) |
|---|---|---|
| Camellia | 2.26 | 0.000309 |
| Feverfew | 1.72 | 0.000088 |
| Camellia-Feverfew 80:20 Blend | 3.73 | |

TABLE 14

Example 2C: Camellia-Feverfew 20:80 Blend
C: Lot#TECJ062904-0184; F: Lot#FF0811K/TL;
C + F: Lot#FFCSWASC02P-0351

| Serum Fraction (1%) | Fold activation | 2-sample t-test vs. blend (p < 0.01 statistically significant) |
|---|---|---|
| Camellia | 2.26 | 0.000041 |
| Feverfew | 2.02 | 0.000003 |
| Camellia-Feverfew 20:80 Blend | 5.02 | |

A constant concentration is used to directly demonstrate that the same level of the dry weight matter in the blended serum fraction has significantly more activity than the level of either of the individual serum fractions alone. This demonstrates that the two dry weight matters in the blend work synergistically together to afford significantly better biological activity. For example in Table 14, Experiment 2C, the individual serum fractions of camellia and feverfew at 1% give 2.26 and 2.02 fold activation respectively, whereas 1% of a 20:80 blend of these serum fractions give a significantly and much greater activation of 5.02 fold. The same is demonstrated for a 50:50 blend (Table 12, Experiment 2A) and 80:20 blend (Table 13, Experiment 2B).

(2) The camellia serum fraction, the feverfew fraction, and combinations can be assessed for IRAK-4 inhibition (all serum fractions analyzed at 0.8% (v/v) of the analytical composition):

TABLE 15

Example 2D: Camellia-Feverfew 50:50 Blend
C: Lot#TECJ062904-0161-01; F: Lot#FF0811K/TL;
C + F: Lot#B02-0712M/OS-0561

| Serum Fraction (0.8%) | % inhibition | 2-sample t-test vs. blend (p < 0.01 statistically significant) |
|---|---|---|
| Camellia | 8 | 0.000604 |
| Feverfew | 9 | 0.000502 |
| Camellia-Feverfew 50:50 Blend | 37.7 | |

TABLE 16

Example 2E: Camellia-Feverfew 80:20 Blend
C: Lot#TECJ062904-0161-01; F: Lot#FF0811K/TL;
C + F: Lot#B02-0719M/OS-0567

| Serum Fraction (0.8%) | % inhibition | 2-sample t-test vs. blend (p < 0.01 statistically significant) |
|---|---|---|
| Camellia | 8 | 0.000045 |
| Feverfew | 9 | 0.000029 |
| Camellia-Feverfew 80:20 Blend | 54.3 | |

A constant concentration is used to directly demonstrate that the same level of the dry weight matter in the blended serum fraction has significantly more activity than the level of either of the individual serum fractions alone. This demonstrates that the two serums in the blend work synergistically together to afford significantly better biological activity. For example in Table 16, Example 2E, the individual serum fractions of camellia and feverfew at 0.8% give 8% and 9% inhibition respectively, whereas 0.8% of a 80:20 blend of these serum fractions gives a significantly and much greater inhibition of 54.3%.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of Embodiments of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A bioactive composition having anti-aging activity, said bioactive composition comprising:
    a. an effective amount of:
        i. a first composition comprising a combination of a camellia serum fraction and a feverfew serum fraction in a weight ratio of 10:90 to about 90:10; and/or
        ii. a second composition comprising a combination of a parsley serum fraction and a kelp serum fraction in a weight ratio of 10:90 to about 90:10.

2. The bioactive composition of claim 1, wherein the first composition comprises:
    a. from about 0.001 wt % to about 15 wt % of the camellia serum fraction; and
    b. from about 0.001 wt % to about 15 wt % of the feverfew serum fraction, wherein the wt % is based on the total weight of the composition.

3. The bioactive composition of claim 2, wherein a weight ratio of the camellia serum fraction to the feverfew serum fraction ranges from about 20:80 to about 80:20.

4. The bioactive composition of claim 2, wherein a weight ratio of the camellia serum fraction to the feverfew serum fraction is about 50:50 to about 80:20.

5. The bioactive composition of claim 2, further comprising a thickening agent.

6. The bioactive composition of claim 1, wherein a weight ratio of the parsley serum fraction to the kelp serum fraction ranges from about 30:70 to about 70:30.

7. The bioactive composition of claim 1, wherein a weight ratio of the parsley serum fraction to the kelp serum fraction is about 50:50.

8. The bioactive composition of claim 1, further comprising a thickening agent.

9. The bioactive composition of claim 1 comprising a combination of the first composition and the second composition.

10. The bioactive composition of claim 9, wherein the first composition comprises:
    a. from about 0.001 wt % to about 15 wt % of the camellia serum fraction, and
    b. from about 0.001 wt % to about 15 wt % of the feverfew serum fraction; and wherein the second composition comprises:
    c. from about 0.001 wt % to about 15 wt % of the parsley serum fraction, and
    d. from about 0.001 wt % to about 15 wt % of the kelp serum fraction, wherein the wt % is based on the total weight of the composition.

11. The bioactive composition of claim 1, wherein said bioactive composition further possesses one or more of the following properties: antioxidant and/or free radical scavenging, inhibition of enzymes associated with skin aging and environmental damage, skin protection, repair of human tissue or skin, UV protection, interruption of an inflammatory cycle, darkening regions of mammalian skin, reducing the appearance of skin hypopigmentation, stimulating one or more steps in melanin synthesis, protection from ozone and/or protection from osmotic shock.

12. The bioactive composition of claim 1, wherein said anti-aging activity comprises hair and/or skin anti-aging activity.

13. The bioactive composition of claim 11 wherein said bioactive composition inhibits enzymes associated with skin aging and environmental damage.

14. The bioactive composition of claim 13 wherein said bioactive composition inhibits melanogenesis enzyme activity.

15. The bioactive composition of claim 13 wherein said bioactive composition inhibits trypsin activity, tyrosinase activity, or both.

16. The bioactive composition of claim 11, wherein said composition increases anti-oxidant activity, free radical scavenging activity, or both.

17. The bioactive composition of claim 1 wherein said bioactive composition interrupts an inflammatory cycle.

18. The bioactive composition of claim 11 wherein said bioactive composition is effective in darkening regions of mammalian skin.

19. The bioactive composition of claim 11 wherein said bioactive composition is effective in reducing the appearance of skin hypopigmentation.

20. The bioactive composition of claim 11 wherein said bioactive composition is effective in stimulate one or more steps in melanin synthesis.

* * * * *